US006465180B1

(12) United States Patent
Bastian et al.

(10) Patent No.: US 6,465,180 B1
(45) Date of Patent: *Oct. 15, 2002

(54) DETECTION OF PREMALIGNANT MELANOCYTES

(75) Inventors: Boris Bastian, San Francisco; Daniel Pinkel, Walnut Creek, both of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/271,619

(22) Filed: Mar. 17, 1999

(51) Int. Cl.[7] .......................... C12Q 1/68; C12P 19/34; C07H 21/04; C12M 1/36
(52) U.S. Cl. .................. 435/6; 435/91.1; 435/91.2; 435/174; 435/283.1; 435/287.2; 536/23.1; 536/24.3; 536/24.33; 536/26.6
(58) Field of Search ................ 435/91.2, 91.1, 435/174, 283.1, 287.2; 536/23.1, 24.33, 26.6, 24.3

(56) References Cited

U.S. PATENT DOCUMENTS

| 5,447,841 A | * | 9/1995 | Gray et al. .................. 435/5 |
| 5,830,645 A | | 11/1998 | Pinkel et al. |
| 5,994,523 A | * | 11/1999 | Kawakami et al. ......... 536/23.5 |

OTHER PUBLICATIONS

Products for Life Science Research, 2000–2001, Sigma–Aldrich, pp. 170 and 322.*
Speicher et al. "Chromosomal gains and losses in uveal melanomas detected by comoparative genomic hybridization" Cancer Research. 1994, 54: 3817–3823.*
Bastian et al., "Chromosomal Gains and Losses in Primary Cutaneous Melanomas Detected by Comparative Genomic Hybridization," *Cancer Res.* (1998) 58: 2170–5.
Day et al., "Malignant melanoma Prognostic Factors 3: Surgical Margins," *J. Dermatol. Surg. Oncol.* (1983) 9:797–801.
Heenan, "A Centimeter There, a Centimeter There: Does it Matter?" *Am. Acad. Dermatol.* (1996) 35:281–2.
Huang et al., "Fluorescence in situ Hybridization Evaluation of Chromosome Deletion Patterns in Prostate Cancer," *Amer. J. Pathology* (Nov. 1996) 149(5): 1565–1573.
Kallioniemi et al., "Comparative Genomic hybridization for Molecular Cytogenetic analysis of Solid Tumors," *Science* (1992) 258: 818–21.
Mishima et al., "Acral Lentiginous melanoma and its Precursor—Heterogeneity of Palmo–Plantar Melanomas," *Pathology* (1985) 17: 258–65.
Wingo, et al., "Cancer Incidence and Mortality, 1973–1995," *Cancer* (1998) 82: 1197–207.
Xu et al., "Detection of 11q13 Amplification as the Origin of a Homogeneously Staining Region in Small Cell Lung Cancer by Chromosome Microdissection," *Genes, Chromosomes & Cancer* (1996) 17: 172–178.

* cited by examiner

Primary Examiner—W. Gary Jones
Assistant Examiner—B J Forman
(74) Attorney, Agent, or Firm—Townsend and Townsend and Crew LLP

(57) ABSTRACT

The present invention provides methods of screening for the presence of premalignant melanocytes in a sample from a patient. The methods comprise contacting a nucleic acid sample from a biological sample from the patient with a probe which binds selectively to a target polynucleotide sequence on a chromosomal region which is amplified in melanoma cells.

16 Claims, 1 Drawing Sheet

DETECTION OF PREMALIGNANT MELANOCYTES

BACKGROUND OF THE INVENTION

Melanoma refers to malignant neoplasms of melanocytes. Its proper diagnosis and early treatment by complete excision is of great importance because advanced melanoma has a poor prognosis and most melanomas are curable if excised in their early stages. In most instances the transformed melanocytes produce increased amounts of pigment so that the area involved can easily be seen by the clinician. When the excision margins of a melanoma are identified based on this macroscopic appearance and no margin of seemingly uninvolved skin is excised, melanoma has the risk of local recurrence.

This has led to the recommendation to remove a safety margin of normal skin that varies from 0.5 to 3 cm depending on the thickness of the primary tumor (Wingo, P. A. et al., *Cancer* 82:1197–207 (1998); Rigel, D. S. et al., *J Am Acad Dermatol* 34:839–47 (1996); McGovern, V. J. et al., *Cancer* 32:1446–57 (1973)). It is obvious that the resulting defect inflicted by the excision can be considerable. If a melanoma measuring 2 cm in diameter that has a thickness of >4 mm is to be excised under the current guidelines, the resulting defect would be 8 cm (2+3+3 cm) in diameter. The closure of excisions with 2–3 cm margins usually require skin grafting and have the potential of adverse consequences such as unsatisfactory cosmetic result, increased morbidity and costs, and sometimes permanent functional impairment. Even with "adequate" safety margins, the melanoma can recur locally.

Obviously, it would be desirable if the margins could be tailored to the needs of the individual patient's tumor. Unfortunately, so far, no technique exists that is able to detect the extent of a tumor accurately. In some types of melanomas the horizontally expanding portion of the tumor mainly consists of single melanocytes along the basal layer of the epidermis. These melanoma types are referred to as lentiginous melanomas. In these, the amount of atypical cells often gradually diminishes towards the margins so that it can be difficult or impossible for the pathologist to determine the border of the melanoma. However, current thinking implies that in most instances, the extent of a melanoma can be assessed by pathology. The fact that the removal of a margin of "healthy" skin reduces the recurrence rate, however, suggests that this skin is actually not healthy but contains residual melanoma which is undetectable by current methods.

The identification of useful means by which morphologically normal premalignant cells that have the capacity to form melanomas can be identified. The present invention addresses these and other needs.

SUMMARY OF THE INVENTION

The present invention provides methods of screening for the presence of premalignant melanocytes in a sample from a patient. The methods comprise contacting a nucleic acid sample from a biological sample from the patient with a probe which binds selectively to a target polynucleotide sequence on a chromosomal region which is amplified in melanoma cells. Usually, the copy number of the target sequence is determined. The nucleic acid sample is typically from morphologically normal cells adjacent to a melanoma lesion in the patient.

In the methods, the probe is contacted with the sample under conditions in which the probe binds selectively with the target polynucleotide sequence to form a stable hybridization complex and the formation of a hybridization complex is detected. The target sequence is selected from the group consisting of 11p15, 11q13, 22q12, 7p, 6p, 1q, 12q14, and 5p.

The nature of the nucleic acid sample is not critical to the invention. In some embodiments, the nucleic acid sample is a metaphase spread or an interphase nucleus. Typically, the probe is labeled e.g. with a fluorescent label. The label may be a direct label. Usually, a reference probe to a second chromosomal region (e.g. a centromere) is used in the methods as an internal control. In these embodiments, the second probe is labeled with a fluorescent label distinguishable from the label on the probe that selectively hybridizes to the target polynucleotide sequence.

In some embodiments, the probe may include repetitive sequences. In this case, the methods may further comprising the step of blocking the hybridization capacity of repetitive sequences the probe Unlabeled blocking nucleic acids comprising repetitive sequences (e.g. Cot-1 DNA) can be contacted with the sample for this purpose.

The nucleic acid hybridization can be carried out in a number of formats. For instance, the hybridization may be an in situ hybridization. In some embodiments, the probe is bound to a solid substrate e.g. in as a member of a nucleic acid array.

Definitions

To facilitate understanding the invention, a number of terms are defined below.

The term "amplicon" as used herein refers to a region of genomic nucleic acid which, when present in altered copy number, is associated with cancer. For example, the invention provides nucleic acid sequences which, when present in aberrant copy number, are associated with melanomas.

An "animal" refers to a member of the kingdom Animalia, characterized by multicellularity, the possession of a nervous system, voluntary movement, internal digestion, etc. An "animal" can be a human or other mammal. Preferred animals include humans, non-human primates, and other mammals. Thus, it will be recognized that the methods of this invention contemplate veterinary applications as well as medical applications directed to humans.

A "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. Cancers include, but are not limited to melanomas, breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testis cancer, biliary tract cancer, small bowel or appendix cancer, salivary gland cancer, thyroid gland cancer, adrenal gland cancer, osteosarcoma, chondrosarcoma, and the like.

The phrase "detecting a cancer" refers to the ascertainment of the presence or absence of cancer in an animal, in this case, melanoma cells or premalignant melanocytes. "Detecting a cancer" can also refer to obtaining indirect evidence regarding the likelihood of the presence of cancerous cells in the animal or to the likelihood or predilection to development of a cancer. Detecting a cancer can be accomplished using the methods of this invention alone, or in combination with other methods or in light of other information regarding the state of health of the animal.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt 2, "Overview of principles of hybridization and the strategy of nucleic acid probe assays,"* Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1–3, Cold Spring Harbor Laboratory, Cold Spring Harbor Press, N.Y., and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C for 15 minutes. An example of a low stringency wash for a duplex of, e.g., more than 100 nucleotides, is 4× to 6×SSC at 40° C. for 15 minutes.

The term "labeled with a detectable composition", as used herein, refers to a nucleic acid attached to a detectable composition, i.e., a label. The detection can be by, e.g., spectroscopic, photochemical, biochemical, immunochemical, physical or chemical means. For example, useful labels include $^{32}P$, $^{35}S$, $^{3}H$, $^{14}C$, $^{125}I$, $^{131}I$; fluorescent dyes (e.g., FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, dioxigenin, or haptens and proteins for which antisera or monoclonal antibodies are available. The label can be directly incorporated into the nucleic acid, peptide or other target compound to be detected, or it can be attached to a probe or antibody that hybridizes or binds to the target. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties. See, e.g., Mansfield (1995) *Mol Cell Probes* 9: 145–156.

The terms "melanoma" or "cutaneous melanoma" refer to malignant neoplasms of melanocytes, which are pigment cells present normally in the epidermis and sometimes in the dermis. There are four types of cutaneous melanoma: lentigo maligna melanoma, superficial spreading melanoma (SSM), nodular melanoma, and acral lentiginous melanoma (AM). Melanoma usually starts as a proliferation of single melanocytes at the junction of the epidermis and the dermis. The cells first grow in a horizontal manner and settle an area of the skin that can vary from a few millimeters to several centimeters. As noted above, in most instances the transformed melanocytes produce increased amounts of pigment so that the area involved can easily be seen by the clinician.

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) *J. Med. Chem.* 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) *Toxicol. Appl. Pharmacol.* 144:189–197. Other synthetic backbones encompasses by the term include methyl-phosphonate linkages or alternating methylphosphonate and phosphodiester linkages (Strauss-Soukup (1997) *Biochemistry* 36: 8692–8698), and benzylphosphonate linkages (Samstag (1996) *Antisense Nucleic Acid Drug Dev* 6: 153–156). The term nucleic acid is used interchangeably with gene, cDNA, mRNA, oligonucleotide primer, probe and amplification product.

The term a "nucleic acid array" as used herein is a plurality of target elements, each target element comprising one or more nucleic acid molecules (probes) immobilized on one or more solid surfaces to which sample nucleic acids can be hybridized. The nucleic acids of a target element can contain sequence(s) from specific genes or clones, e.g. from the regions identified here. Other target elements will contain, for instance, reference sequences. Target elements of various dimensions can be used in the arrays of the invention. Generally, smaller, target elements are preferred. Typically, a target element will be less than about 1 cm in diameter. Generally element sizes are from 1 µm to about 3 mm, preferably between about 5 µm and about 1 mm. The target elements of the arrays may be arranged on the solid surface at different densities. The target element densities will depend upon a number of factors, such as the nature of the label, the solid support, and the like. One of skill will recognize that each target element may comprise a mixture of nucleic acids of different lengths and sequences. Thus, for example, a target element may contain more than one copy of a cloned piece of DNA, and each copy may be broken into fragments of different lengths. The length and complexity of the nucleic acid fixed onto the target element is not critical to the invention. One of skill can adjust these factors to provide optimum hybridization and signal production for a given hybridization procedure, and to provide the required resolution among different genes or genomic locations. In various embodiments, target element sequences will have a complexity between about 1 kb and about 1 Mb, between about 10 kb to about 500 kb, between about 200 to about 500 kb, and from about 50 kb to about 150 kb.

The terms "nucleic acid sample" or "sample of human nucleic acid" as used herein refers to a sample comprising human DNA or RNA in a form suitable for detection by hybridization or amplification. Typically, it will be prepared from a tissue sample from a patient who has or is suspected of having melanoma. The sample will most usually be prepared from tissue surrounding a melanoma tumor.

In many instances, the nucleic acid sample will be a tissue or cell sample prepared for standard in situ hybridization methods described below. The sample is prepared such that individual chromosomes remain substantially intact and typically comprises metaphase spreads or interphase nuclei prepared according to standard techniques. Alternatively, the nucleic acid may be isolated, cloned or amplified. It may be, e.g., genomic DNA, mRNA, or cDNA from a particular chromosome, or selected sequences (e.g. particular promoters, genes, amplification or restriction fragments, cDNA, etc.) within particular amplicons or deletions disclosed here.

The nucleic acid sample may be extracted from particular cells or tissues, e.g. melanocytes. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves from cell cultures, cells from tissue culture and other media in which it may be desirable to detect chromosomal abnormalities or determine amplicon copy number. In some cases, the nucleic acids may be amplified using standard techniques such as PCR, prior to the hybridization. The sample may be isolated nucleic acids immobilized on a solid.

A "premalignant melanocyte" is a morphologically normal cell that has the capacity to form a malignant melanoma tumor. Such cells are typically found adjacent to a melanoma tumor. As used here, "adjacent" means less than 5 cm, usually less than 3 cm, from the nearest a typical cell in the tumor.

The term "probe" or a "nucleic acid probe", as used herein, is defined to be a collection of one or more nucleic acid fragments whose hybridization to a sample can be detected. The probe may be unlabeled or labeled as described below so that its binding to the target or sample can be detected. The probe is produced from a source of nucleic acids from one or more particular (preselected) portions of the genome, e.g., one or more clones, an isolated whole chromosome or chromosome fragment, or a collection of polymerase chain reaction (PCR) amplification products. The probes of the present invention are produced from nucleic acids found in the regions described herein. The probe or genomic nucleic acid sample may be processed in some manner, e.g., by blocking or removal of repetitive nucleic acids or enrichment with unique nucleic acids. The word "sample" may be used herein to refer not only to detected nucleic acids, but to the detectable nucleic acids in the form in which they are applied to the target, e.g., with the blocking nucleic acids, etc. The blocking nucleic acid may also be referred to separately. What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767–773; Johnston (1998) *Curr. Biol.* 8: R171-R174; Schummer (1997) *Biotechniques* 23: 1087–1092; Kern (1997) *Biotechniques* 23: 120–124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

"Providing a nucleic acid sample" means to obtain a biological sample for use in the methods described in this invention. Most often, this will be done by removing a sample of cells from an animal, but can also be accomplished by using previously isolated cells (e.g. isolated by another person), or by performing the methods of the invention in vivo.

"Tissue biopsy" refers to the removal of a biological sample for diagnostic analysis. In a patient with cancer, tissue may be removed from a tumor, allowing the analysis of cells within the tumor.

DESCRIPTION OF THE SPECIFIC EMBODIMENTS

Figure 1:
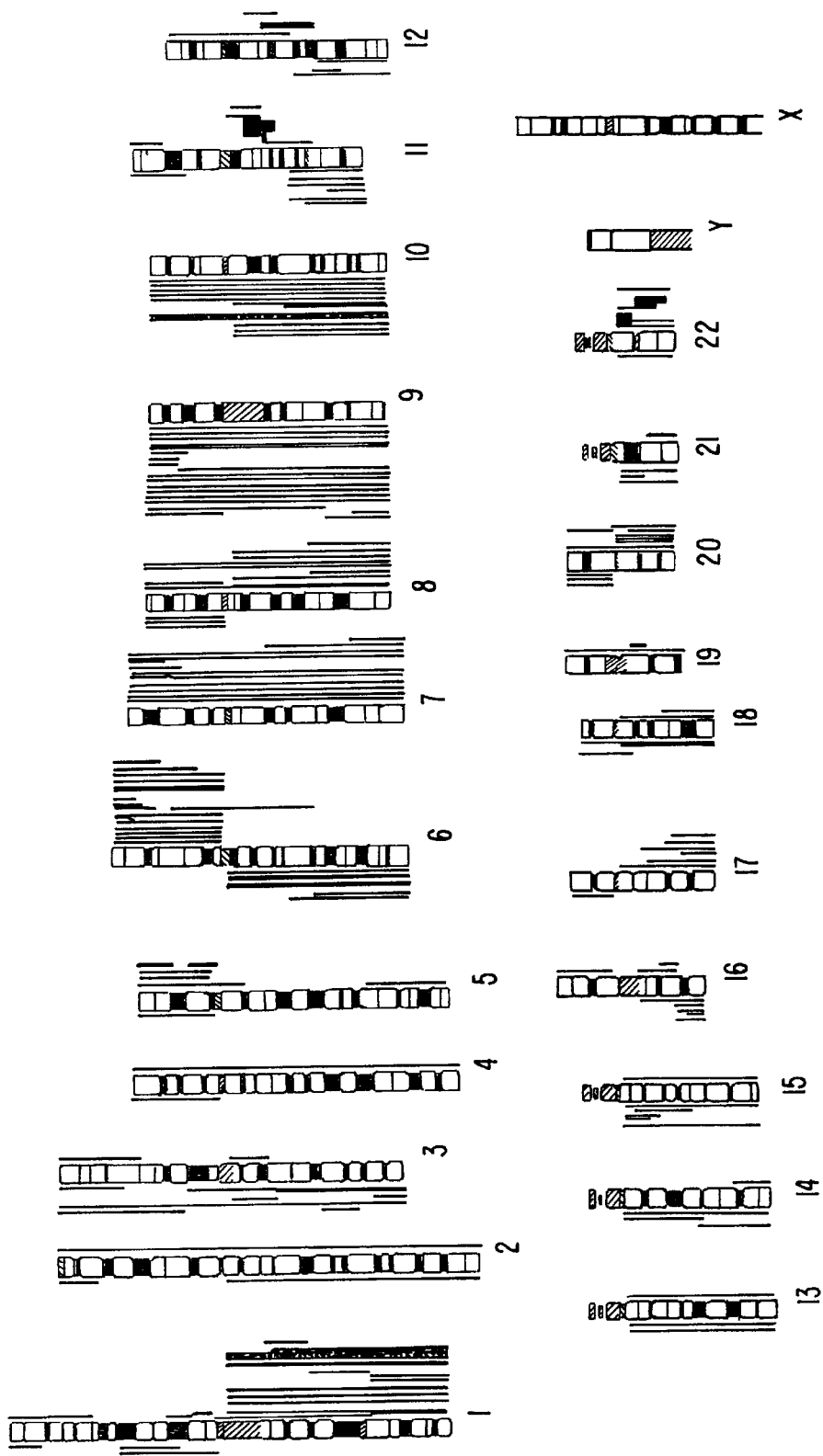
FIG. 1 shows chromosomal localization of DNA-sequence copy number changes in 15 AMs and 15 SSMs detected by CGH. Lines to the right of the chromosome ideograms represent gains, lines to the left represent losses. Bold lines indicate amplifications.

Melanoma incidence has significantly increased over the last five decades (Wingo, P. A. et al., *Cancer* 82:1197–207 (1998); Rigel, D. S. et al., *J Am Acad Dermatol* 34:839–47 (1996)). It has long been noted that the clinical and histological presentation of melanoma is not entirely homogenous but shows patterns of association between anatomic location, type of sun exposure, age, as well as ethnicity. These patterns led to a proposal of a classification of different types of primary cutaneous melanoma: lentigo maligna, superficial spreading, nodular and acral melanoma (McGovern, V. J. et al., *Cancer* 32:1446–57 (1973)). However, since certain histologic features of these melanoma types overlap and no independent prognostic differences among the types have been discovered (Krementz, E. T. et al., *Ann Surg* 195:632–45 (1982); Panizzon, R. et al., *Schweiz Med Wochenschr* 112:612–8 (1982); Brauninger, H. et al., *Hautarzt* 45:529–531 (1994)), the justification for such a classification has become controversial (Ackerman, A. B. et al., *Hum Pathol* 17:438–40 (1986); Flotte, T. J. et al., *Hum Pathol* 17:441–2 (1986)). Thus there seems to be a growing tendency among clinicians and pathologists dealing with melanoma to regard primary cutaneous melanoma as a single disease entity. Furthermore, human melanoma cell lines used in basic research usually are not identified based on the type of primary melanoma they are derived from. Thus clinical practice and basic research studies on melanoma that do not take into account potential differences among types of melanoma may be predisposed to overlook associations that pertain only to certain types and thereby hamper the progress of research.

The invention is based on this observation that markers of regions frequently found to be gained in melanoma (chromosomes 11p15, 11q13, 22q12, 7p, 6p, 1q, 12q14, 5p) can be used to detect morphologically normal but genomically aberrant cells (referred to here as premalignant melanocytes) at the margins of excision specimens with a higher sensitivity than conventional methods.

Detection of Copy Number

In one embodiment, the presence of, or premalignant melanocytes is evaluated simply by a determination of copy number of the regions identified here. Typically, the regions evaluated are 11p15, 11q13, 22q12, 7p, 6p, 1q, 12q14, and 5p. Methods of evaluating the copy number of a particular gene or chromosomal region are well known to those of skill in the art.

Hybridization-based assays

Preferred hybridization-based assays include, but are not limited to, traditional "direct probe" methods such as Southern Blots or In Situ Hybridization (e.g., FISH), and "comparative probe" methods such as Comparative Genomic Hybridization (CGH). The methods can be used in a wide variety of formats including, but not limited to substrate—(e.g. membrane or glass) bound methods or array-based approaches as described below.

In situ hybridization assays are well known (e.g., Angerer (1987) *Meth. Enzymol* 152: 649). Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. The preferred size range is from about 200 bp to about 1000 bases, more preferably between about 400 to about 800 bp for double stranded, nick translated nucleic acids.

In some applications it is necessary to block the hybridization capacity of repetitive sequences. Thus, in some embodiments, human genomic DNA or Cot-1 DNA is used to block non-specific hybridization.

In Comparative Genomic Hybridization methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Hybridization protocols suitable for use with the methods of the invention are described, e.g., in Albertson (1984) *EMBO J.* 3: 1227–1234; Pinkel (1988) *Proc. Natl. Acad. Sci. USA* 85: 9138–9142; EPO Pub. No. 430,402; *Methods in Molecular Biology, Vol.* 33: *In Situ Hybridization Protocols,* Choo, ed., Humana Press, Totowa, N.J. (1994), etc. In one particularly preferred embodiment, the hybridization protocol of Pinkel et al. (1998) *Nature Genetics* 20: 207–211 or of Kallioniemi (1992) *Proc. Natl Acad Sci USA* 89:5321–5325 (1992) is used.

The methods of this invention are particularly well suited to array-based hybridization formats. For a description of one preferred array-based hybridization system see Pinkel et al. (1998) *Nature Genetics,* 20: 207–211.

Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606–614; Jackson (1996) *Nature Biotechnology* 14:1685; Chee (1995) *Science* 274: 610; WO 96/17958.

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No: 5,807,522). This patent describes the use of an automated systems that taps a microcapillary against a surface to deposit a small volume of a biological sample. The process is repeated to generate high density arrays. Arrays can also be produced using oligonucleotide synthesis technology. Thus, for example, U.S. Pat. No. 5,143,854 and PCT patent publication Nos. WO 90/15070 and 92/10092 teach the use of light-directed combinatorial synthesis of high density oligonucleotide arrays.

In another embodiment the array, particularly a spotted array, can include genomic DNA, e.g. overlapping clones that provide a high resolution scan of the amplicon corresponding to the region of interest. Amplicon nucleic acid can be obtained from, e.g., MACs, YACs, BACs, PACs, P1s, cosmids, plasmids, inter-Alu PCR products of genomic clones, restriction digests of genomic clone, cDNA clones, amplification (e.g., PCR) products, and the like.

In various embodiments, the array nucleic acids are derived from previously mapped libraries of clones spanning or including the target sequences of the invention, as well as clones from other areas of the genome, as described below. The arrays can be hybridized with a single population of sample nucleic acid or can be used with two differentially labeled collections (as with an test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

For example, methods for immobilizing nucleic acids by introduction of various functional groups to the molecules is known (see, e.g., Bischoff (1987) *Anal. Biochem.*, 164: 336–344; Kremsky (1987) *Nucl. Acids Res.* 15: 2891–2910). Modified nucleotides can be placed on the target using PCR primers containing the modified nucleotide, or by enzymatic end labeling with modified nucleotides. Use of glass or membrane supports (e.g., nitrocellulose, nylon, polypropylene) for the nucleic acid arrays of the invention is advantageous because of well developed technology employing manual and robotic methods of arraying targets at relatively high element densities. Such membranes are generally available and protocols and equipment for hybridization to membranes is well known.

Target elements of various sizes, ranging from 1 mm diameter down to 1 $\mu$m can be used. Smaller target elements containing low amounts of concentrated, fixed probe DNA are used for high complexity comparative hybridizations since the total amount of sample available for binding to each target element will be limited. Thus it is advantageous to have small array target elements that contain a small amount of concentrated probe DNA so that the signal that is obtained is highly localized and bright. Such small array target elements are typically used in arrays with densities greater than $10^4/cm^2$. Relatively simple approaches capable of quantitative fluorescent imaging of 1 $cm^2$ areas have been described that permit acquisition of data from a large number of target elements in a single image (see, e.g., Wittrup (1994) *Cytometry* 16:206–213).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait (1984) Oligonucleotide Synthesis: A Practical Approach, IRL Press, Wash., D.C.). Quartz cover slips, which have at least 10-fold lower autofluorescence than glass, can also be silanized.

Alternatively, probes can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith (1992) *Science* 258: 1122–1126). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

In one particularly preferred embodiment, probe nucleic acid is spotted onto a surface (e.g., a glass or quartz surface). The nucleic acid is dissolved in a mixture of dimethylsulfoxide (DMSO) and nitrocellulose and spotted onto aminosilane coated glass slides. Small capillaries tubes can be used to "spot" the probe mixture.

A variety of other nucleic acid hybridization formats are known to those skilled in the art. For example, common formats include sandwich assays and competition or displacement assays. Hybridization techniques are generally described in Hames and Higgins (1985) *Nucleic Acid Hybridization, A Practical Approach*, IRL Press; Gall and Pardue (1969) *Proc. Natl. Acad. Sci. USA* 63: 378–383; and John et al. (1969) *Nature* 223: 582–587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected.

Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE-T at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.1 to about 0.5 mg/ml DNA (e.g., cot-1 DNA). The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background membranes can be used (see, e.g., Chu (1992) *Electrophoresis* 13:105–114). The sensitivity for detection of spots ("target elements") of various diameters on the candidate membranes can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., membranes, glass, fused silica) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Labeling and Detection of Nucleic Acids

In a preferred embodiment, the hybridized nucleic acids are detected by detecting one or more labels attached to the sample or probe nucleic acids. The labels may be incorporated by any of a number of means well known to those of skill in the art. Means of attaching labels to nucleic acids include, for example nick translation or end-labeling (e.g. with a labeled RNA) by kinasing of the nucleic acid and subsequent attachment (ligation) of a nucleic acid linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence. Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

Amplification-based Assays

In another embodiment, amplification-based assays can be used to measure copy number. In such amplification-based assays, the nucleic acid sequences act as a template in an amplification reaction (e.g. Polymerase Chain Reaction (PCR). In a quantitative amplification, the amount of amplification product will be proportional to the amount of template in the original sample. Comparison to appropriate (e.g. healthy tissue) controls provides a measure of the copy number of the desired target nucleic acid sequence. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et aL (1990) *PCR Protocols, A Guide to Methods and Applications*, Academic Press, Inc. N.Y.).

Other suitable amplification methods include, but are not limited to ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al (1989) *Proc. Natl. Acad Sci. USA* 86: 1173), and self-sustained sequence replication (Guatelli et al. (1990) *Proc. Nat. Acad. Sci. USA* 87: 1874).

Detection of Gene Expression

As indicated below, a number of oncogenes are found in the regions of amplification disclosed here. Thus, oncogene activity can be detected by, for instance, measuring levels of the gene transcript (e.g. mRNA), or by measuring the quantity of translated protein.

Detection of Gene Transcripts

Methods of detecting and/or quantifying t gene transcripts using nucleic acid hybridization techniques are known to those of skill in the art (see Sambrook et al. supra). For example, a Northern transfer may be used for the detection of the desired mRNA directly. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target mRNA. In another preferred embodiment, the gene transcript can be measured using amplification (e.g. PCR) based methods as described above for directly assessing copy number of the target sequences.

Detection of Expressed Protein

The "activity" of the target onocgene can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, nucleic acids for detecting the target sequesences and other hybridization probes and/or primers. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

This example describes detection of regions of chromosomal abnormality in acral melanoma.

Acral melanoma (AM) is one type of melanoma that probably shows the most striking features, that separates it from other, more common form of cutaneous melanoma. It develops on palmar, plantar and subungual skin (Arrington, J. H. d. et al., *Am J Surg Pathol* 1:131–343 (1977)), sites of predilection that have little exposure to sunlicht and are protected from ultraviolet radiation (UV) by a thick stratum corneum. This makes it unlikely that (UV) plays a role in the pathogenesis of AM. Interestingly, AM is the most common type of melanoma in dark-skinned peoples (Coleman, W. P. d. et al., *Arch Dermatol* 116:773–6 (1980); Kukita, A. et al., *J Invest Dermatol* 92:21OS-213S (1989)), although its overall incidence appears to be similar across all racial groups (Elwood, J. M. *J Invest Dermatol* 92:214S-221S (1989)). In a previous study of 32 randomly selected primary cutaneous melanomas using comparative genomic hybridization (CGH) (Kallioniemi, A. et al. *Science* 258:818–21 (1992)) it was noted that gene amplifications occurred infrequently in melanomas but that acral melanomas might have frequent amplifications (Bastian, B. C. et al., *Cancer Res* 58:2170–5 (1998)). Here we demonstrate that acral melanoma constitutes a distinct type of primary cutaneous melanoma that is characterized by a unique type of genomic instability expressed by frequent high-level amplifications of small genomic regions that target oncogenes.

Results

Matched-pair Analysis of AM and SSM Using CGH

Our initial study of a random selection of primary cutaneous melanoma (Bastian, B. C. et al., *Cancer Res* 58:2170–5 (1998)) included a single case of AM that differed from the other cases by the presence of multiple high-level amplifications involving small chromosomal subregions. To investigate a potential difference in the pattern of chromosomal aberrations between AM and SSM, the most frequent type of melanoma, we selected a total of 15 pairs of these two types of melanoma. To exclude any bias by patient age and tumor thickness that we had previously found to correlate with the total number of aberrations, both groups were matched for age and tumor thickness. The mean age and tumor thickness in the AM group was 72.2 years (range 44–87 years) and 4.6 mm (range 1.3–14 mm), while it was 70.8 years (range 40–84) and 5.0 mm (range 1.2–20 mm) in the SSMs.

The aberrations detected by CGH are summarized in FIG. 1. Similarities between the two groups are readily apparent. The most frequent changes in both groups matched our earlier findings (Bastian, B. C. et al., *Cancer Res* 58:2170–5 (1998)). Losses of chromosomes 9p and 10q occurred in 10/15 (67%) and 7/15 (47%) of the AMs and 9/15 (60%) and 7/15 (47%) of the SSMs, respectively. In contrast, gains of chromosome 7p, 5p and losses of chromosome 6q were found more frequently in the AM group (53% vs. 13%, 33% vs. 0%, and 47% vs. 7% respectively). However, these differences were not statistically significant given that a total of 39 comparisons (i.e., the arms of all autosomes) were performed.

Significant differences between AM and SSM were found when the total number and types of aberrations in both groups were analyzed. First, as shown in table 1, the total number of aberrations was significantly higher in the acral melanomas. This was true for gains, losses, and most clearly with amplifications (see Methods for definition). Every acral melanoma had at least one amplification, while many had multiple amplifications (mean 1.9). In the AM group, a total of 29 amplifications in the AM involved at least 14 separate loci. Most frequently, amplifications involved chromosomes 11q and 22q. However, as can be seen in FIG. 1, chromosomal regions 5p15, 5p13, 12q13–22, and 16q21–22 were amplified in more then one tumor. In contrast, only two amplifications were found in the entire set of SSMs, one in each of two tumors.

TABLE 1

|     | Losses | Gains  | No. of amplifications | Total No |
| --- | ------ | ------ | --------------------- | -------- |
| AM  | 76     | 67     | 29                    | 162      |
| ssm | 49     | 33     | 2                     | 84       |
| P   | 0.01   | 0.0004 | 0.0000002             |          |

In situ Detection of Amplifications by FISH

In order to obtain information on the copy number and tissue distribution of the amplifications, we performed dual-color FISH on tissue sections of the tumors that showed amplifications by CGH. The ploidy of the tumors was assessed by using reference probes for regions that had normal copy number by CGH. A total of 61 FISH measurements encompassing 18 different loci were performed in the 17 cases in which amplifications were detected by CGH.

FISH indicated that if the CGH ratio exceeded 1.3 for a subregion of a chromosomal arm the tumors contained very high copy number at that locus. For example, in two cases (AM61 and AM63) CGH showed tumor:reference ratios at chromosomal band 11q13 of 1.5 and 1.3), respectively. The corresponding average number of FISH signals determined with a probe mapping to 11q13.2 (RMC11p005) ranged, depending on the location within the tumor, from 6 to >20 signals in AM61 and was relatively stable at 7 signals in case AM63. In both cases the reference probes indicated a near diploid karyotype, i.e. a signal count similar to normal keratinocytes of the section. The difference in apparent copy number found by FISH and CGH is due to two major factors. First, CGH measures the average copy number of sequences within the group of cells that are analyzed. Thus contamination of the specimen by normal cells and heterogeneity of amplification level within the tumor, will result in ratios that underestimate the highest level that is present. However, CGH also underestimates the level of amplification when the amplified regions are small (Piper, J. et al. *Cytometry* 19:10–26 (1995)). This is due to the complex packing of the DNA in the metaphase chromosomes to which the probes are hybridized. This latter reason is probably the dominant factor in these measurements since in some cases FISH probes, chosen based on the apparent position of a CGH peak, missed the peak of the amplified region. This is exemplified by case AM104 which had amplifications of the distal portions of chromosomes 5p and 6p by CGH. A probe mapping to 6p25-pter (RMC06B005) showed 1–2 signals per nucleus, indicating that the amplicon did not involve the entire distal p-arm of chromosome 6. The distal arm of chromosome 5p was amplified to equal levels by CGH and revealed an average of 10 copies per nucleus with a probe for chromosome 5p15 (RMC05B3326A).

In most cases, there was limited heterogeneity in the level of amplification within the tumor. If a radial part of the neoplasm was present, its cells had signal counts that were not significantly different from those found in the cells of the invasive part. Only one case (AM51) showed high nucleus to nucleus variations of signals with probes for chromosome 7p21 (RMC07B3078A) and chromosome 12q14 (12B014), i.e., variations from 4 to over 40 and 6 to over 20 signals, respectively. In this case, cells with high copy numbers of the 12q14 probe were more frequent at the deeper parts of the tumor whereas signal numbers of 7p21 varied over the entire tumor.

Interestingly, in five cases of AM isolated cells with high signal counts could be detected in the basal layer of the epidermis up to 5 mm away from the invasive portion of the tumor. In 4 cases this finding correlated with the presence of scattered, single melanocytes that histologically showed slightly enlarged, hyperchromatic nuclei. Case AM59 had amplifications involving chromosomes 5q11.2-pter, 11p15-pter, and 16q22-qter. The H-ras oncogene is a likely target of the 11p15 amplicon and we performed FISH using a green-labeled probe that contained the H-ras gene (RMC11B022). A red-labeled probe for chromosome 11q that was unchanged by CGH (RMC 11P014) was used as a reference. Many single cells with more than 10 green signals and 2–3 reference signals could be seen in the basal layer over a distance of 5 mm from the actual tumor. An immunostain with an antibody that detects wild type and mutant (val-12) H-ras showed strong H-ras expression by the melanocytes within that region. As can be seen in the labeled cells did not have atypical nuclei. Outside of the area where the cells with the amplification were found, no H-ras expression within basal melanocytes could be detected.

Mutation Analysis of H-ras

H-ras is the probable target of the amplification of chromosome 11p15 of case AM59. To support this notion, we searched for mutations at codons 12, 13 and 61 of H-ras by sequence analysis. We found a G→T mutation of codon 12 at position 34 leading to Gly12Cys transition. No wild-type sequence was detected. Of the other cases, informative sequence data was obtained from 22 tumors (12 AMs and 10 SSMa). Case AM61 had a heterozygous A→G mutation at codon 61 leading to a Gln61Arg transition. The remaining 21 cases had wild-type sequences.

Detection of Amplifications in AM In-situ

The finding of amplifications in all AM and the demonstration of amplifications in the in-situ portion of several AMs by FISH suggested that amplifications occur early in the progression of AM. In this event, it would be expected to find amplifications in AM that have not progressed to an invasive stage. Therefore, we selected five additional cases of AM in-situ. Those lesions could not be studied by CGH, because it is not possible to collect sufficient tumor cells without significant contamination by normal cells. Instead, we used F SH with markers for the regions that were most frequently amplified in the invasive AM, namely 11q13) (RMC11P008) and 22q12 (RMC22P004). Three of the five AM in-situ showed amplification of 11q13, and one case had an additional amplification of 22q12. The average number of the amplified signals ranged from six in one case to over ten in the two other cases. Reference probes did not show increased copy numbers.

Discussion

Our data demonstrates a significantly higher frequency of gene amplifications in acral melanomas (AM) than in other types of cutaneous melanoma (100% vs. 15%). Other human cancers such as glioblastoma, neuroblastomas, and breast cancer have been shown to have amplifications in up to 50% of cases (Brodeur, G. M. et al., (eds. Vogelstein, B. & Kinzler, K, W.) (McGraw-Hill, New York, 1998)). Since amplifications in other cancers can indicate a poor prognosis (Seeger, R. C. et al., *N Engl J Med* 313:1111–6 (1985)), it is currently thought that amplifications represent a late event in human cancer (Lengauer, C. et al., *Nature* 396:643–649 (1998)). In contrast, the detection of amplifications in AM in-situ demonstrates early development of amplifications in the progression of this cancer type.

The occurrence of at least one (mostly several) amplification of a chromosomal subregion in all sixteen invasive AM studied so far (including the index case of AM (Bastian, B. C. et al., *Cancer Res* 58:2170–5 (1998))) as well as at least three of the five in-situ AM suggests that gene amplification plays a fundamental role in this cancer. It is tempting to speculate that a specific defect occurring early in tumorigenesis leads to the amplification of genes important in melanocyte transformation. The frequent amplifications could thus represent a novel type of chromosomal instability that drives tumor progression, analogous to aneuploidy due to inactivation of mitotic spindle checkpoints in colorectal cancer (Lengauer, C., et al., *Nature* 386:623–7 (1997)). In support of this hypothesis is the fact that the amplicons in our cases frequently contain genes that belong to established pathways in the control of melanocyte growth or cell growth in general. The most frequently amplified region (11 q13) contains the fibroblast growth factors (FGF) 3 and 4, and cyclin D1. Basic FGF is a well-known and highly effective mitogen for melanocytes (Halaban, R., et al., *In Vitro Cell Dev Biol* 23:47–52 (1987)), and can serve as an autocrine growth factor in human melanoma (Halaban, R., et al., *Oncogene Res* 3:177–86 (1988)). Platelet derived growth factor (PDGF) has been shown to have autocrine mitogenic properties as well (Behl, C. et al., *Biochem Bioshys Res Commun* 193:744–51 (1993), and PDGFA and PDGFB map to 7p22 and 22q12–13, both regions that are frequently gained or amplified in our AMs. Endothelin-1 another potent growth factor for melanoma (Yada, Y. et al, *J Biol Chem* 266:18352–7 (1991)) maps to 6p23–34, a region that is commonly gained. Other amplicons harbour potential downstream targets of these factors such as H-ras (1p 13.2), H-ras (11p15), and positive regulators of the cell cycle CDK4 (12q14), ETF4 (16q22) and cyclin E (19q13). Based on these associations and our finding, of a mutated H-ras within the amplicon, we feel that it is reasonable to expect that the other amplified regions do not represent random genomic "noise", but will be found to contain genes important in melanoma development. A higher resolution picture of the structure of the amplicons is currently being obtained by the use of CGH to microarrays of mapped clones (Pinkel, D. et al., *Nat. Genet.* 20:207–211 (1998)).

Most acral melanomas exhibit a radial growth phase in which the neoplastic melanocytes are arranged as solitary units along the basal layer of the epidermis. This pattern is referred to as lentiginous and contrasts with the more frequent finding of single cells above the dermoepidermal junction in SSM. Therefore, AMs have also been called acral lentiginous melanoma. However, not all AMs exhibit a lentiginous growth pattern and indeed some believe that SSM and nodular melanoma also occur on acral skin (Feibleman, C. E. et al., *Cancer* 46:2492–504 (1980); Sondergaard, K. et al., *Acta Pathol Microbiol Scand [A]* 88:275–83 (1980)). The distinction between the patterns of intraepidermal involvement in the various types of melanoma is far from absolute, and both AM and lentigo maligna melanoma often show areas of nested growth and cells above the basal layer above invasive foci. This finding may account for some of the difficulty that pathologists have in reliably separating the types of melanoma by light microscopy. Twelve of our AMs had a lentiginous radial growth phase and in two cases, no radial growth phase was represented in the blocks so that no such classification was possible. One case had a predominantly nested radial growth phase. Amplifications were found in all AMs, indicating that the amplifier phenotype is present independent of the growth pattern. All AM cases of the present series were located on the foot; however the index case that had three amplifications (Bastian, B. C. et al., *Cancer Res* 58:2170–5 (1998)) was a subungual melanoma from the finger. This indicates that the amplifier phenotype is not restricted to plantar melanomas. Although it seems likely that the occurrence on glabrous skin is the common denominator of AM, future studies are warranted to define their spectrum more completely.

Until now, controversy existed whether the subtle increase in the number of melanocytes without or with slight atypia beyond the unambiguously recognizable radial tumor parts in AM represent in-situ melanoma or "activated melanocytes" (Mishima, Y. et al., *Pathology* 17:258–65 (1985)). Our finding of amplifications in single melanocytes up to 5mm from the invasive tumor parts by FISH clearly suggests that this phenomenon represents melanoma in-situ rather than a reactive phenomenon. Melanoma has a well-documented tendency to recur locally when not excised with a margin of normal skin (Day, C. L., Jr. et al., *J Dermatol Surg Oncol* 9:797–801 (1983)). As FISH detected aberrant cells well beyond the area where atypical cells were obvious histologically, it is possible that these "satellite" cells represent the source of recurrence. Future studies are needed to determine whether this observation can help resolve the controversy over the size of resection margins in melanoma (Heenan, P. J. *J Am Acad Dermatol* 35:281–2 (1996)).

Our data indicates qualitative differences in the type of chromosomal abnormality in AM compared to other types of melanoma. In contrast, when the overall pattern of chromosomal gains and losses shows is considered, AMs and SSMs exhibit more similarities than differences. Few genomic regions such as chromosomes 5p, 6q, and 7p showed different frequencies of involvement. This similarity of the pattern of aberrations could be interpreted as an indication that genes operating in the same pathways/checkpoints are affected in melanoma subtypes, but that it is the mode of gene activation that differs. Gene amplification could be the predominant mode of oncogene activation in AM whereas in other types it may be mutations and rearrangements. Tumor progression of subtypes might later converge to a common final pathway, explaining the similar clinical course of melanoma subtypes once the disease metastasizes. If this assumption is correct, the "amplifier phenotype" in AM may provide a unique opportunity to identify biologically relevant genes in melanoma progression because the affected genomnic regions are highlighted by small amplifications.

Material and Methods

Study Populations 15 cases that had been archived under the diagnosis of ALM were randomly selected from the archive material of the Department of Dermatolocy, University of Würzburg, the Dermatopathology Section of the Departments of Patholocy and Dermatology, and the Melanoma Center of the University of California, San Francisco. Two acral melanomas (AM) were from the toe, 10 from the sole, and three were from the foot without further specification. By histology, twelve AM were of the acral lentiginous type, two were unclassifiable because the radial portion of the tumors were not represented in the specimen, and one had overlapping features with SSM. As controls fifteen cases that were matched for patient age (±5 years) and tumor thickness (<1.5 mm, 1.5–4.0 mm, and >4.0 mm and had been archived as SSM were retrieved. Histological re-assessment showed typical features of SSM in all fifteen controls. No tumor had significant solar elastosis indicative of severe chronic sun damage.

For the analysis of AM in-situ, five tumors were selected from the database of the Melanoma Center at the University of California, San Francisco.

Comparative Genomic Hybridization

DNA Extraction. 30 $\mu$m sections were cut from the paraffin blocks, with a 5 $\mu$m section for H&E every 5 sections. The unstained 30 $\mu$m sections were placed on glass slides and an area of interest was microdissected without de-paraffinizing. Microdissection was carried out manually under a dissecting microscope. Depending on the size of the tumor 3–20 unstained sections were used and regions with a high density of tumor cells were separated from normal cells. The dissected tumor parts were collected in tubes and de-paraffinized by washing with xylene and ethanol. DNA extraction and labeling was performed as published by Isola et al. 9 Isola, J. et al., *Am J Pathol* 145:1301–8 (1994)). Briefly, tissue was incubated until complete digestion (3 days) with proteinase K (Life Technologies, Inc., Gaithersburg, Md.) in a 50 mM Tris pH8.5, 1 mM EDTA, 0.5% Tween 20 buffer. DNA was extracted with phenol-chloroform-isoamylalcohol (25:24:1, v/v), precipitated with 7.5 m ammonium acetate and 100% ethanol, and resuspended in water. The amount of DNA obtained ranged from 2 to 12 $\mu$g.

CGH. All tumors were measured both with the tumor DNA labeled with fluorescein-12-dUTP (Dupont Inc., Boston, Mass.), and reference DNA with Texas red-5-dUTP ("standard" labeling), and with the labeling reversed. Labeling was performed by Nick translation. Nick translation conditions were adjusted so that the probe fragment size after labeling ranged between 800 and 1500 bp. The hybridization mixture consisted of 200–1000 ng of labeled tumor DNA, 200 ng inversely labeled normal human reference DNA from peripheral blood lymphocytes, and 25 3c, human Cot-1 DNA (Life Technologies, Inc., Gaithersburg, Md.) dissolved in 10 $\mu$l hybridization buffer (50% formamide, 10% dextrane sulfate, and 2×SSC, pH 7.0). Hybridization was carried out for 2–3) days at 37° C. to normal metaphases (Kallionlemi, A. et al., *Proc. Natl. Acad. Sci. U.S.A.* 91:2156–60 (1994)). All samples were investigated with a single a batch of metaphase slides. Slides were washed three times in a washing solution (50% formamide in 2×SSC, pH) at 45° C., once in PN buffer (0.1 M NaH$_2$PO$_4$, 0.1 M Na$_2$FIPO$_4$, and 0.1% Nonidet P40, pH 8.0), and once in distilled water (both 10 minutes at room temperature). After hybridization, slides were counterstained with 4,6-diamino-2-phenylindole in an anti-fade solution. Hybridization quality was evaluated as published previously (Bastian, B. C. et al., Cancer Res 58:2170–5 (1998)). Digital images were collected from five metaphases with a CCD camera (Microimager 1400, Xiliix Technologies, Vancouver, British Columbia, Canada) on a standard fluorescence microscope. The average tumor/reference fluorescence ratios along each chromosome were calculated with custom CGH analysis software. Measurements were made on at least 4 copies of each autosome.

Controls and Threshold Definitions. Normal DNA and DNA from tumor cell lines with known aberrations were used as controls. We regarded a region as aberrant when 1) either the standard labeling or the reverse labeling resulted in a tumor/reference fluorescent ratios <0.80 or >1.2 or 2) both the standard and the reverse labeling resulted in a tumor:reference fluorescent ratios <0.85 or >1.15.

Fluorescence In-situ Hybridization (FISH)

Dual-color FISH was carried out on tissue sections of the tumors that showed an amplification by CGH. Probes mapping to amplified regions and reference probes for regions that were unchanged by CGH analysis were selected from the Laboratories resource (http://rmc-www.lbl.gov). Probes were labeled with Cy3 (Amersham, Arlincton Heights, Ill.) or with Digoxigenin (Boehringer Mannheim, Indianapolis Ind.) by nick translation. 6 $\mu$m sections were mounted on positively charged glass slides (Fisher Scientific, Pittsburgh, Pa.), deparaffinized, and hydrated by decreasing strength ethanol. Sections were incubated for 2–4 min in 1M sodium thiocyanate at 80° C., in 4 mg/ml Pepsin in 0.2 N HCl at 37° C. for 4–8 min, dehydrated by increasing strength ethanol and air-dried. Slides were denatured in 70% formamide, 2×SSC pH 7.0 for 5 min at 72° C., and dehydrated again in a graded ethanol series. 2.5 to 25 ng of each of the labeled probes together with 20 $\mu$g Cot-1 DNA (Life Technologies, Inc., Gaithersburg, Md.) were dissolved in 10 $\mu$l hybridization buffer (50% formamide, 10% dextrane sulfate, and 2×SSC, pH 7.0) and denatured for 10 min at 72° C. Hybridization was carried out for 48–72 hours at 37° C. Slides were washed three times in washing solution (50% formamide in 2×SSC, pH 7.0) at 45° C., once in 2×SSC at 45° C., once in 2×SSC at room temperature (RT), and once in 0.1% TritonX100 in 4×SSC at RT. Subsequently, sections were incubated with 10% BSA in 4×SSC in a moist chamber at 37° C., and then with a FITC labeled anti-digoxigenin antibody (Boehringer Mannheim, Indianapolis Ind.) diluted in 4×SSC with 10% BSA. Sections were counterstained with 4,6-diamino-2-phenylindole (Sigma, St. Louis, Mo.) in an anti-fade solution.

In all experiments keratinocytes of the epidermis adjacent to the lesion were used as internal controls. As the hybridization was carried out on sections of 6 $\mu$m thickness, many nuclei were not fully represented in the slide. For counting hybridization signals, we selected nuclei that appeared minimally truncated when the focus of the microscope was slightly altered. The nuclear signal counts in keratinocytes ranged from mean values of 1.6–1.9. Tumor cells that had average signal counts within that range were regarded as near diploid.

Definition of Amplifications

Based on CGH measurements regions were called amplified if the tumor/reference ratio of a distinct segment of a chromosomal arm exceeded 1.5 or if the ratio elevation highlighted a sharply demarcated segment of a chromosomal arm. In most cases both criteria were met, however, in some tumors the amplified chromosomal segment was too narrow to yield a ratio >1.5. Several tumors of the ALM group had copy number increases exceeding a tumor/reference ratio of 1.5 that involved the entire chromosome. These changes were not considered as amplifications.

Based on the FISH experiments, regions exhibiting at least three times the average signal number of the reference probe were called amplified.

Immunohistochemistry

Immunostaining for human c-H-ras was performed using a mouse monoclonal antibody against recombinant c-H-ras (val-12) (Dako Corp., Calpinteria, Calif., Code No. M637, dilution 1:100) according to standard procedures with the avidin-biotin immunoperoxidase method using diaminobenzidine as a chromogen.

DNA Sequence Analysis

H-ras codon 12 primers were 5'AGGAGACCCTGTAGGAGGA-3' (forward) and 5'-CGCTAGGCTCACCTCTATAGTG-3' (reverse) and codon 61 primers were 5'-CTGCAGGATTCCTACCGGA-3' and 5'-ACTTGGTGTTGTTGATGGCA-3'. PCR was carried out in a Gene Amp PCR System 9700 Thermal Cycler (Perkin Elmer) in 25 $\mu$l reaction volumes. Each PCR reaction contained 3.5 mM MgCl$_2$, 0.2 mM dNTP, 0.625 U Taq Gold Polymerase (Perkin Elmer), 1×PCR Buffer II, 0.5 $\mu$M each of forward and reverse primer, and 50–300 ng of genomic DNA. PCR cycling conditions were as follows: 95° C. for 15 min followed by 35 cycles of 95° C. for 15 sec, 55° C. for 30 s and 72° C. for 60 seconds, and a final hold at 72° C. for 10 minutes.

Prior to sequencing, PCR products were purified using the PCR product Presequencing kit (Amersham, Arlington Heights, Ill.) to remove excess primers and nucleotides. Fluorescent DNA sequencing was carried out using Big Dye dye terminator sequencing chemistry (PE Applied Biosystems). Briefly, 30–50 ng of purified PCR product and 3.2 pmoles of sequencing primer were used for sequencing in a 15 $\mu$l reaction according to the manufacturer's instructions. The sequencing products were purified using a Sephadex G50 column, dried in a vacuum concentrator and resuspended in 3 $\mu$l of gel loading buffer (83% deionized formamide, 17% gel loading dye) (PE Applied Biosystems). 0.5 $\mu$l of the sample was then loaded on a denaturing sequence gel on an ABI automated DNA sequencer. Data was analyzed using the Sequence Analysis 3.0 software from PE Applied Biosystems and all samples were sequenced in both forward and reverse directions to confirm the presence/absence of mutations.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of screening for the presence of premalignant melanocytes in a sample from a patient, the method comprising:

contacting a nucleic acid sample from morphologically normal cells less than 5 cm from the nearest atypical cell in a melanoma lesion from the patient with a probe which binds selectively to a target polynucleotide sequence on a chromosomal region which is amplified in melanoma cells and is a region selected from the group consisting of 11p15, 11q13, 22q12, 7p, 6p, 1q, 12q14, and 5p, wherein the probe is contacted with the sample under conditions in which the probe binds selectively with the target polynucleotide sequence to form a stable hybridization complex;

detecting the formation of a hybridization complex, and determining the presence in the sample of an increase in copy number of the chromosomal region to which the probe selectively binds, thereby detecting the presence of the premalignant melanocytes in the sample.

2. The method of claim 1, wherein the nucleic acid sample is a metaphase spread or an interphase nucleus.

3. The method of claim 1, wherein the probe is labeled.

4. The method of claim 3, wherein the label is a fluorescent label.

5. The method of claim 4, wherein the fluorescent label is FITC.

6. The method of claim 3, wherein the probe is labeled with digoxigenin or biotin.

7. The method of claim 3, wherein the label is a direct label.

8. The method of claim 1, further comprising contacting the sample with a reference probe to a second chromosomal region.

9. The method of claim 8, wherein the second chromosomal region is a centromere.

10. The method of claim 8, wherein the reference probe is labeled with a fluorescent label and is distinguishable from the probe that selectively hybridizes to the target polynucleotide sequence.

11. The method of claim 1, wherein the step of detecting the hybridization complex comprises determining the copy number of the target polynucleotide sequence.

12. The method of claim 1, further comprising the step of blocking the hybridization capacity of repetitive sequences in the nucleic acid sample.

13. The method of claim 12, wherein unlabeled blocking nucleic acids comprising repetitive sequences are contacted with the sample.

14. The method of claim 13, wherein the unlabeled blocking nucleic acids are Cot-1 DNA.

15. The method of claim 1, wherein probe is bound to a solid substrate.

16. The method of claim 15, wherein the probe is a member of an array.

* * * * *